(12) United States Patent
Gerges

(10) Patent No.: US 8,529,574 B2
(45) Date of Patent: Sep. 10, 2013

(54) CUTTING GUIDE FOR REMOVAL OF CAM LESION

(75) Inventor: Justin Joseph Gerges, Waldwick, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 265 days.

(21) Appl. No.: 13/166,107

(22) Filed: Jun. 22, 2011

(65) Prior Publication Data

US 2012/0330318 A1 Dec. 27, 2012

(51) Int. Cl.
*A61B 17/58* (2006.01)
*A61B 17/60* (2006.01)
*A61F 2/00* (2006.01)

(52) U.S. Cl.
USPC .................. 606/89; 606/79; 606/87; 606/96; 606/86 R

(58) Field of Classification Search
USPC ................ 606/86 R, 87, 89, 79, 82, 80, 180, 606/96; 600/227–234
See application file for complete search history.

(56) References Cited

U.S. PATENT DOCUMENTS

| | | | |
|---|---|---|---|
| 5,468,243 A | 11/1995 | Halpern | |
| 5,486,180 A | 1/1996 | Dietz et al. | |
| 5,653,714 A | 8/1997 | Dietz et al. | |
| 6,503,255 B1 | 1/2003 | Albrektsson et al. | |
| 6,554,838 B2 | 4/2003 | McGovern et al. | |
| 7,445,595 B2 | 11/2008 | Brannon | |
| 7,601,155 B2 | 10/2009 | Petersen | |
| 7,695,477 B2 | 4/2010 | Creger et al. | |
| 2004/0153083 A1* | 8/2004 | Nemec et al. | 606/86 |
| 2007/0249967 A1 | 10/2007 | Buly et al. | |
| 2007/0299452 A1 | 12/2007 | Curry | |
| 2009/0022015 A1 | 1/2009 | Harrison | |
| 2009/0163923 A1 | 6/2009 | Flett et al. | |

FOREIGN PATENT DOCUMENTS

WO 2010033473 A2 3/2010

* cited by examiner

*Primary Examiner* — Andrew Yang
*Assistant Examiner* — Olivia C Chang
(74) *Attorney, Agent, or Firm* — Lerner, David, Littenberg, Krumholz & Mentlik, LLP

(57) ABSTRACT

A cutting guide for removing a lesion from a neck area of a femur has a body having first and second side rails. The first and second side rails are spaced in a direction perpendicular to the head neck axis of the femur when mounted adjacent a neck of the femur. A third rail has ends slidably mounted on the first and second side rails. The third rail can be resiliently deformable toward a surface of the neck of the femur. A carrier element slidably mounted on the third rail for movement therealong between the first rail and the second rail. A bone cutting tool such as a burr is mountable in the carrier element. The first and second rails are connected by a proximal rigid cross-member at first ends thereof adjacent a femoral head. The cross-member is shaped to conform to an outer surface of the femoral neck adjacent the femoral head. The second ends of the first and second rails are connected by a member having a mounting element thereon adjacent a trochanter area of the femur. The mounting element may be a bore for receiving a bone screw or bone pin.

13 Claims, 5 Drawing Sheets

CUTTING GUIDE FOR REMOVAL OF CAM LESION

BACKGROUND OF THE INVENTION

This invention relates to an instrument and method for removing a cam lesion from the neck of a femur.

Femoral acetabular impingement is a condition of too much moving contact between the femur and the rim of the acetabulum during movement of the hip joint. There are two forms of contact between the neck and head of the femur and the acetabulum under the category of femoral acetabular implant. One form is called cam impingement and the other pincer impingement. The cam form occurs when the femoral head and neck is shaped so that it impinges on an otherwise normal rim of the acetabulum. This abnormal contact between the head and neck of the femur and the acetabular rim generates pain. The pincer form of impingement occurs when the rim of the acetabulum is enlarged to provide excessive coverage of the femoral head so that the rim impinges on a normally shaped head or neck of the femur upon movement of the hip joint. Again this contact causes pain in the patient. Often these two problems occur simultaneously. Usually the deformities in both the neck and head of the femur and of the rim of the acetabulum face anteriorly in the anterior-superior quadrant.

Because the area of contact between the bone of the neck and head of the femur and the acetabular cartilage occurs over a wide area, usually the cartilage area involved in cam impingement is larger than in pincer impingement.

Cam impingement can be caused by an osseous bump or lesion on the femoral head-neck junction. In the past, arthroscopic debridement of the femoral neck has been performed to remove cam lesions. Alternately, a surgical procedure in which an anteriolateral bump is removed with an osteotome is used to restore the concave contour of the head-neck junction. In addition, the femoral head may be rounded by smoothing the surface with a burr. In either of these procedures the resections are performed by hand without the use of any instrumentation designed to facilitate the quick and accurate removal of bone tissue.

BRIEF SUMMARY OF THE INVENTION

One aspect of the present invention is the provision of a resection instrument that is in the form of a saddle that can be placed in the head-neck area of the femur spaced above an area having a cam lesion. The instrument has an arched cross member which connects a pair of generally proximally-distally extending rails, which cross member sits against the rim of the acetabulum adjacent the base of the part-spherical femoral head. The two rails which are spaced by the cross member straddle the head/neck area of the femur and have mounted thereon a third moveable rail which may be slid between first and second ends of the first and second rails with the cross member acting as a stop in the proximal direction. An additional cross member may be provided extending between the first and second rails acting as a stop in the distal direction. Alternately the first and second rails may be spaced leg portions of a continuous flexible u-shaped rail. These leg portions may be spaced so that movement of the third rail causes the leg portions to expand this limiting movement towards a base of the u-shaped rail. On the third rail there is mounted a tool carrying member or carriage member which can move along the third rail between the first and the second rails. Thus, a cutting tool mounted on the tool carrier can resect bone in an area defined between the first and second rails and the proximal and distal cross members. This allows for removal of an entire lesion from the neck of the femur.

To allow for the bone to be resected at a variable depth in the cutting area the third rail is flexible. Thus, this multiple track system allows for three-dimensional motion of the cutting tool with the outside tracks and cross members acting as a limit for movement of the cutting tool such as a burr.

The proximal cross member of the cutting guide that sits against the femoral head in the area of the acetabular rim serves two purposes. First it serves as a tool for aligning the guide with the proper region of the acetabulum and femoral neck. Secondly, the region of the cross member that lines up with the acetabular rim extends a predetermined distance from the rim serving as a stop for the tool carrier so that it does not approach the labrum or the femoral head and articular cartilage. The more distal cross member opposite the acetabular rim can have a fixation element for fixing the instrument to the femoral neck which fixation element prevents the back end from moving in a fashion that would lead to uncontrolled burring of the femoral neck. Such a fixation element can be attached to the base of the u-shaped continuous rail which extends between the first and second leg portions The instrument can be designed based on patient-specific CT or MRI data. The CT data can define the rim of the acetabulum and the extent of the cam lesion so that the instrument may be properly sized and the maximum depth of flexion of the third rail can be set.

Once the cutting guide is properly aligned with the cam lesion and acetabular rim, the user can move the cutting burr through all possible desired forward and backward movements as well as movements into the femoral neck. This allows the user to remove the area of bone on the femoral neck that results in impingement. This can be accomplished while protecting the labrum and articular cartilage.

To utilize the cutting instrument it can be placed through the Smith-Peterson interval between the TFL and SARTOROUS including lining the edge of the proximal cross member with the acetabular rim so that the first and second rails normal to the acetabular rim straddle the cam lesion. The surgeon will then attach a burr and drive system within the movable tool carrier mounted on the movable third rail to remove the cam lesion by tracking back and forth and around the lump on the femoral neck.

A similar device can be deployed arthroscopically. The device can have a spring loaded mechanism that forces the first and second rails to a position where they are normal to the proximal cross member that sits along the acetabular rim. A burr fits into a carriage or tool carrier on the moveable third rail as described above allowing the surgeon to move the burr back and forth without having to worry about resecting or damaging articular cartilage because the proximal cross member of the device lines up with the acetabular rim and extends distantly in line with the base of the femoral head.

DETAILED DESCRIPTION

Figure 1:
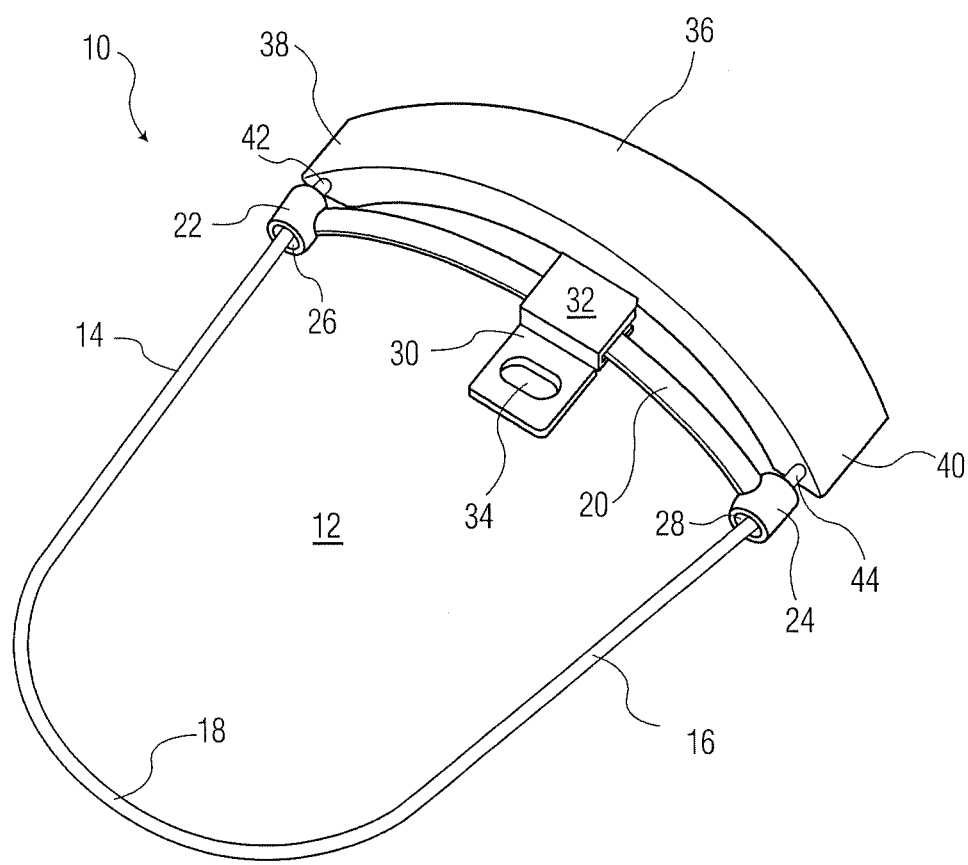
FIG. 1 is an isometric view of the cutting guide for the removal of a cam lesion mounted on a femur of the present invention.
Figure 9:
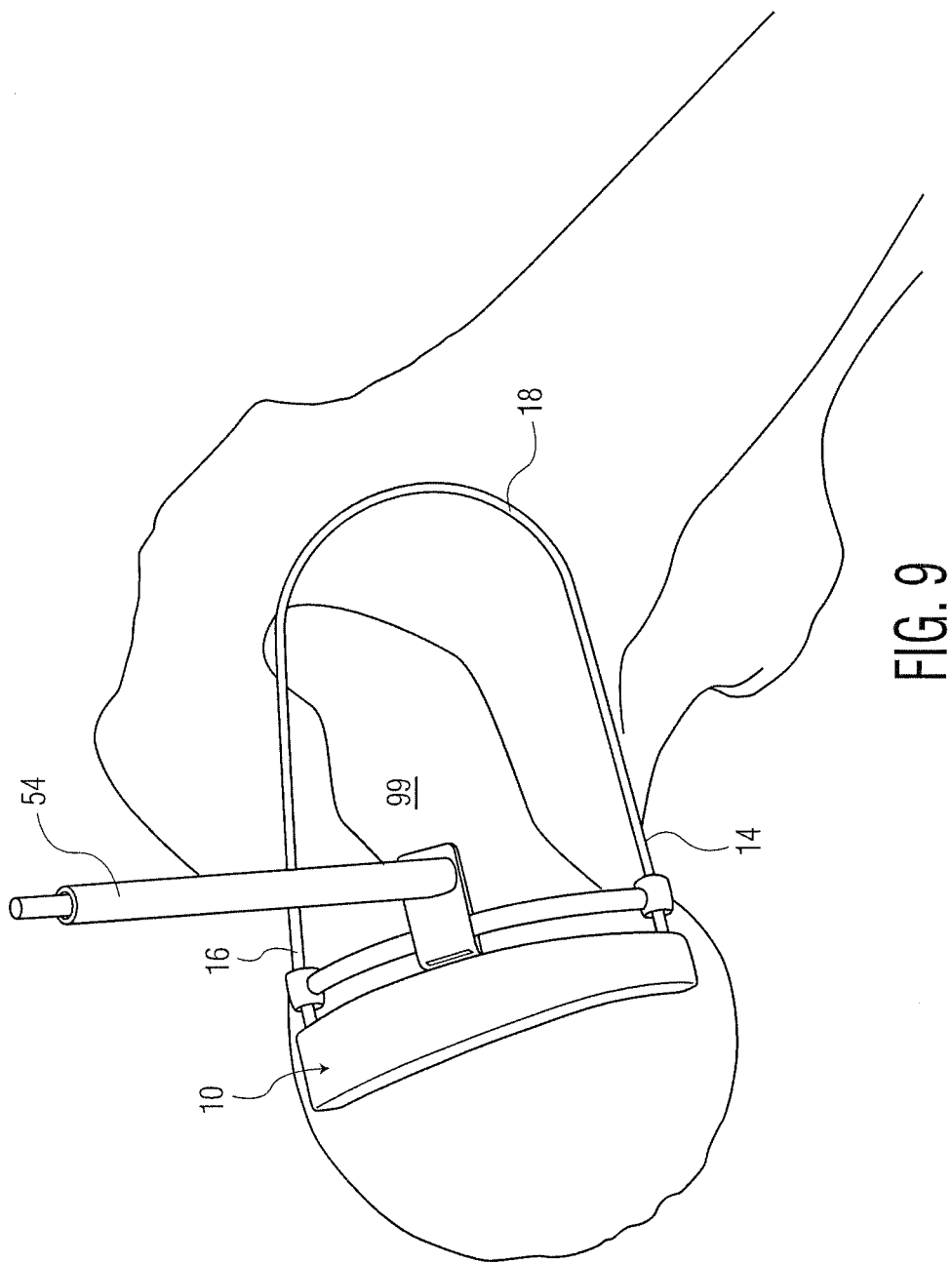
FIG. 9 shows the cutting guide of FIG. 1 mounted on a proximal femur with a cutting tool thereon.

Referring to FIGS. 1 and 9, there is shown a cutting guide generally denoted as 10 for removing a lesion 10a, such as a cam lesion, from a neck area of a femur 11. Cutting guide 10 includes a frame or body 12 composed of a pair of rail portions or legs 14 and 16 which may be in the form of a u-shaped rod member having a base portion 18. Rail portions or legs 14, 16 may taper towards one another in the generally proximal-distal direction when the frame 12 is mounted on the neck of femur 11. Base 18 may be arcuate and connect distal ends of legs 14, 16. A third rail 20 is slidably mounted on first and second rails 14, 16 via a pair of bushings 22 and 24. Bushings 22 and 24 have cylindrical bores 26 and 28 for receiving legs 14 and 16 respectively. In use bores 26 and 28 lie along an axis which extends along an axis generally parallel to the head and neck axis of the femur.

Third rail member 20 may be in the form of an arc with its concave portion facing the neck of the femur. The arcuate portion may be deformed resiliently towards the femur. Rail 20 may have a generally rectangular cross-section with the longest part of the rectangle extending in a direction generally parallel to the axis of bores 26 and 28. This facilitates the resilient deformation of third rail 20 towards and away from the neck of the femur.

Third rail 20 further includes a tool carrier or carriage 30 which is slidably mounted on third rail 20 and movable along rail 20 from a first end adjacent bushing 22 to a second end adjacent bushing 24. Carrier 30 includes a mounting member 32 having an aperture slidably receiving rail 20. If rail 20 has a rectangular cross-section obviously the aperature would be rectangular. Tool carrier 30 also includes an opening 34 to receive a cutting portion of a cutting tool as will be discussed below.

Figure 2:
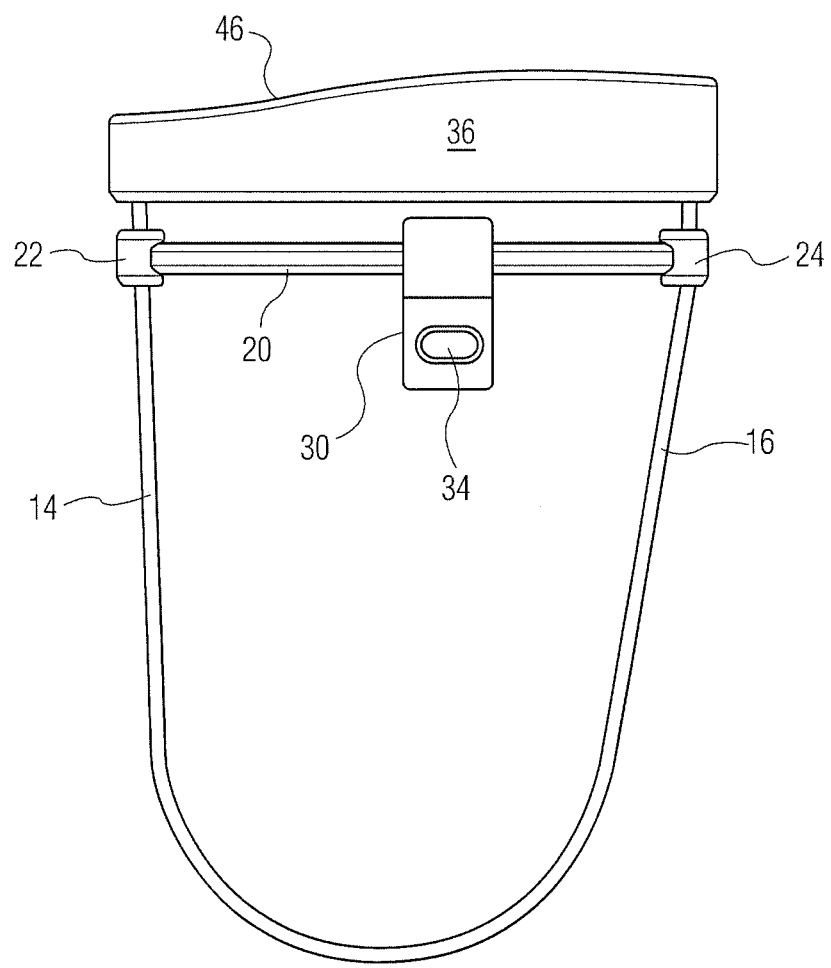
FIG. 2 is a top view of the cutting guide of FIG. 1.

An arcuate cross-member 36 in the form of an arched plate is provided which plate has ends 38 and 40 to which ends 42 and 44 of rail portions 14 and 16 are fixed. The attachment may be by welding portions 14 and 16 which could extend through cross-member 36 and spot welded on the proximal side thereof. In use, cross-member 36 is located adjacent the head of the femur and sits against the rim of the acetabulum and has a shape to conform generally with the outer surface of the head/neck where it enters the acetabulum femur. As best seen in FIG. 2, cross member 36 may have a proximal surface 46 which varies in thickness to better conform with the anatomy of the acetabulum and femoral head. The thinner area is preferably located on the femur. The proximal-distal width of cross-member 36 is sized to prevent the cutting tool 50 from contacting the cartilage of the acetabulum.

Figure 3:
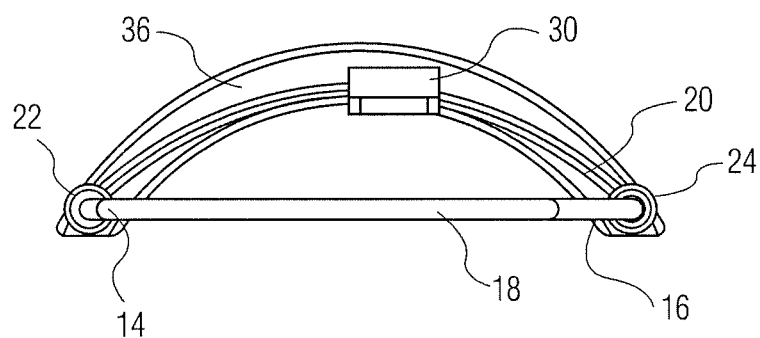
FIG. 3 is a front elevation view showing the tool carriage of the present invention in a first position.
Figure 4:
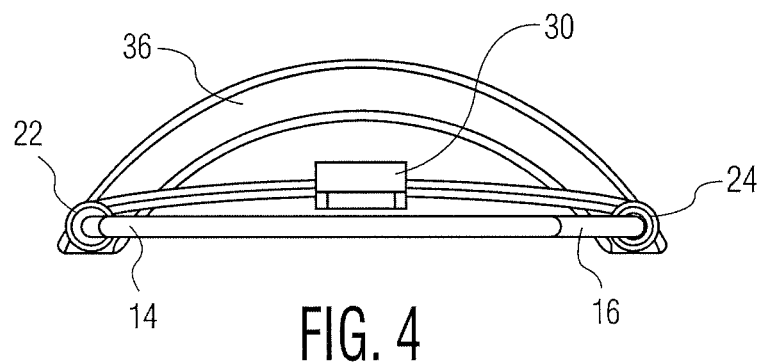
FIG. 4 is a front elevation view of FIG. 2 showing the tool carrier in a second position adjacent the femoral neck.

Referring to FIG. 3, there is shown an elevation view of the cutting guide with carrier 30 spaced from the plane defined by the u-shaped rod forming rails 14, 16 and base 18. This shows the relaxed or free position of rail 20 at which time tool carrier 30 is spaced at or above any bony protuberance or cam lesion on the bone. Referring to FIG. 4, there is shown carrier 30 in a second position in which rail 20 has been depressed by a surgeon so that tool carrier 30 is now closer to the plane of the rod forming legs 14 and 16 and in a position to resect bone. In this position a cutting tool mounted in tool carrier 30 would be in a position to contact a cam lesion.

Figure 5:
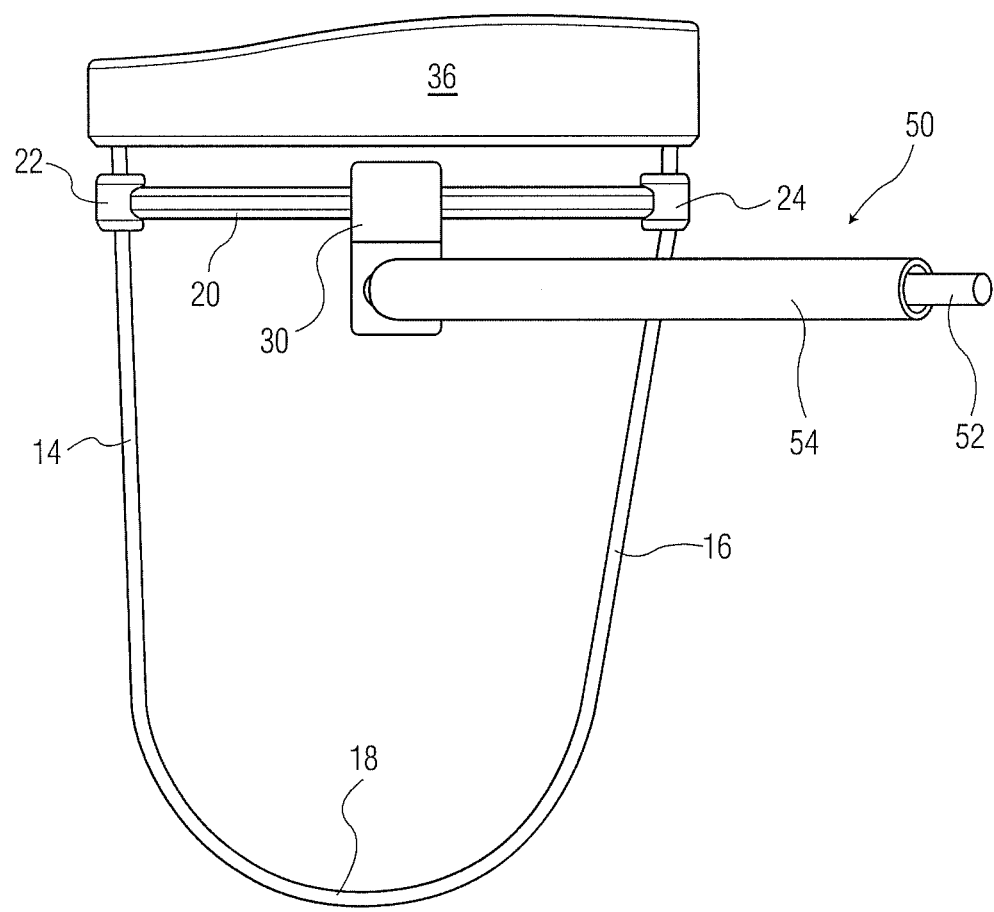
FIG. 5 is the cutting guide of FIG. 2 including a cutting tool mounted in the tool carrier of the present invention.
Figure 6:
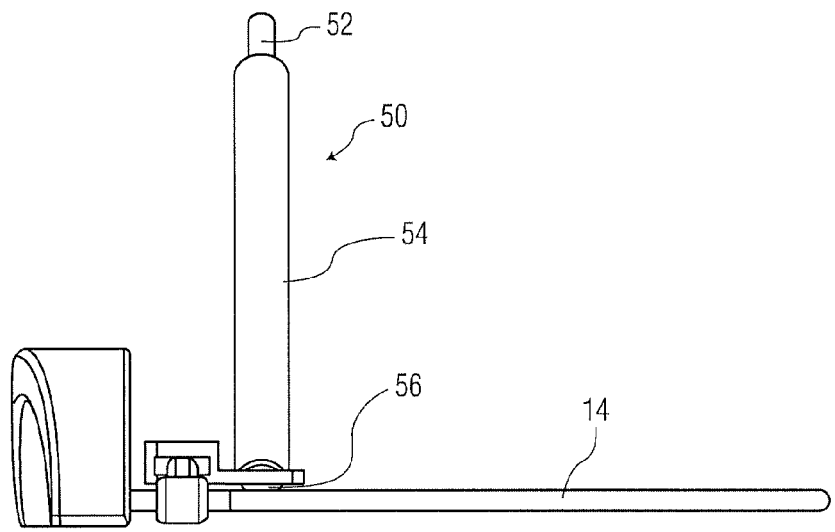
FIG. 6 is a side elevation view of the cutting guide of FIG. 5.

Referring to FIGS. 5 and 6 there is shown a cutting tool generally denoted 50 which includes a drive shaft 52 and an outer protective sleeve 54. Sleeve 54 protects tissue from the rotating drive shaft 52. Cutting tool 50 includes a cutting tip 56 which may be in the form of a burr mill or reamer. Of course, any tool tip suitable for cutting bone may be used.

Figure 7:
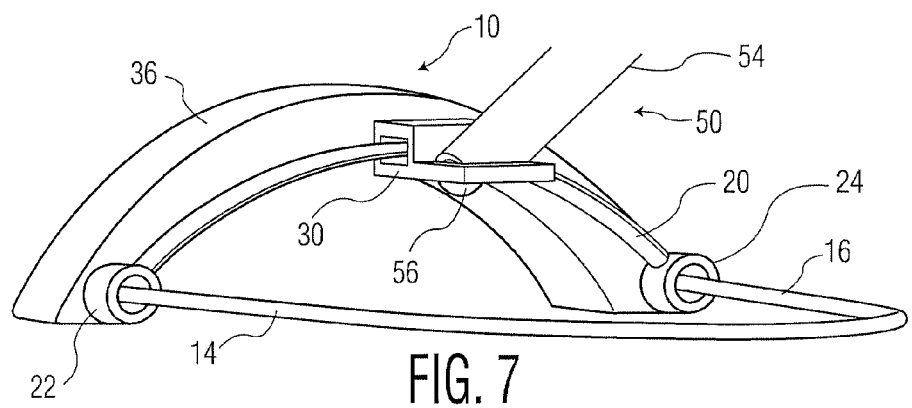
FIG. 7 is a perspective view of the cutting guide of FIG. 5 including the tool mounted in the tool carrier with the tool carrier located in the first position.
Figure 8:
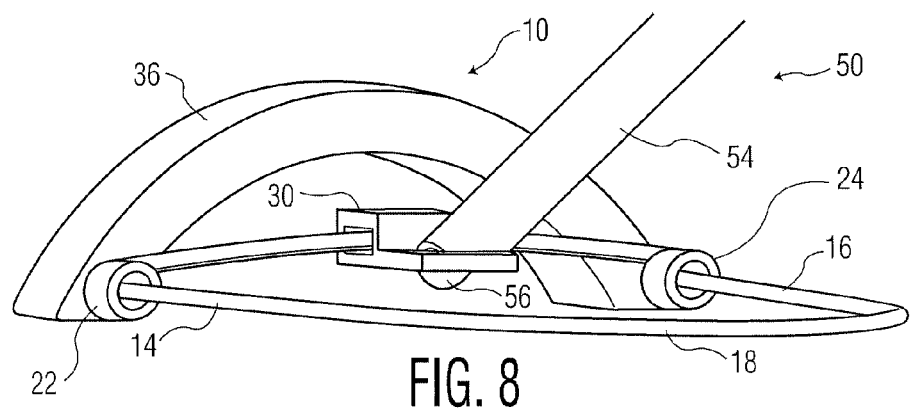
FIG. 8 is a perspective view of the cutting guide with the tool carriage in the second position closer to the neck of a femur.

Referring to FIGS. 7 and 8 which show perspective views of the cutting guide 10 and cutting tool 50 shown in FIGS. 3 and respectively, it can be seen that the surgeon locates the cutting guide 10 on the neck of the femur with cross-member 36 around the neck adjacent and preferably in contact with the femoral head. Thus, legs 14 and 16 extend generally distally towards the inter-trochanteric region of the femur. In its relaxed position, rail 20 has a length greater than the distance between rail portions 14 and 16 and thus is arched away from the surface of the femoral neck. The surgeon then inserts cutting tool 50 such that the burr 56 extends through opening 34 and deforms flexible rail 20 towards the neck of the femur, as shown in FIG. 8, to contact any cam lesion present. It can be seen that carrier 30 can be moved along rail 20 between rail portions 14 and 16. Additionally, bushings 22 and 24 may be slid along rail portions 14 and 16 respectively thus allowing the tip of a burr 56 to traverse the entire extent of the femoral neck area on which cutting tool 10 is mounted. This allows the surgeon to controllably remove sufficient malformed bone to enhance the range of motion between the femoral neck and the acetabulum.

It can be seen that as the bushings 22 and 24 are moved along converging rail portions 14 and 16 towards the base portion 18 the rod making up portions 14, 16 and 18 will expand in width on moving proximally to distally in a direction of the femoral neck-head axis 60. This is due to the tapered form of legs 14 and 16 towards base member 18. As the tension in portions 14, 16 and 18 increase as bushings 22 and 24 are moved distally, the bushings bind on leg portions 14 and 16 thereby limiting the distal motion of cutting burr 56 in the distal direction. Movement in the proximal direction in the femoral neck is limited by cross-member 36.

While rails 14, 16 and 18 are shown as a continuous flexible wire or rod base 18 could be a plate like element similar to cross-member 36.

FIG. 9 shows the cutting guide 10 mounted on a proximal femur 11 and positioned to remove a cam lesion 10a. Cutting tool 54 which has a rotating burr (not shown) can be manipulated by the surgeon to remove lesion 10a. Because rails 14 and 16 are small in cross-section they can be easily flexed to enable the surgeon to resect bone outside the initial relaxed perimeter of the rails and remove an entire cam lesion 99.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cutting guide for removing a lesion from a neck area of a femur comprising:
 a body having first and second side rails, the first and second side rails are spaced in a direction transverse to a central axis of a head and neck of a femur when mounted adjacent the neck of the femur;

a third rail having ends slidably mounted on a respective one of the first and second side rails, the third rail being resiliently deformable toward a surface of the neck of the femur; and a tool carrier slidably mounted on the third rail for movement therealong between the first rail and the second rail.

2. The cutting guide as set forth in claim 1 further comprising a bone cutting tool mountable in the carrier.

3. The cutting guide as set forth in claim 2 wherein the cutting tool is a burr.

4. The cutting guide as set forth in claim 2 wherein ends of the first and second rails are connected by a cross member at first ends thereof adjacent a femoral head.

5. The cutting guide as set forth in claim 4 wherein the cross member is shaped to conform to an outer surface of the femoral neck adjacent the femoral head.

6. The cutting guide as set forth in claim 4 wherein second ends of the first and second rails are connected by a mounting element adjacent a trochanter area of the femur.

7. The cutting guide as set forth in claim 6 wherein the mounting element includes a bore for receiving a bone screw or bone pin.

8. The cutting guide as set forth in claim 1 wherein the first and second rails are curved to generally conform to an outer surface of the femoral neck.

9. The cutting guide as set forth in claim 1 wherein the first and second rails have a length capable of extending from a rim of an acetabulam to a trochanter area of the femur.

10. The cutting guide as set forth in claim 1 wherein the first and second rails are spaced legs of a flexible u-shaped rod.

11. The cutting guide as set forth in claim 10 wherein the first and second legs converge towards one another on moving in the proximal to distal direction.

12. A method of removing a bone lesion from the neck or head of a femur comprising:

mounting a cutting guide having a body comprising first and second side rails, the first and second side rails are spaced in a direction transverse to a central axis of a head and neck of a femur when mounted adjacent the neck of the femur, a third rail having ends slidably mounted on a respective one of the first and second side rails, the third rail being resiliently deformable toward a surface of the neck of the femur, a tool carrier slidably mounted on the third rail for movement therealong between the first rail and the second rail; and moving the tool on the tool carrier on the cutting guide and into engagement with a bone lesion on a femoral neck or head and resecting the lesion.

13. The method as set forth in claim 12 further comprising locating the stop surface a distance from an acetabulum to prevent the tool from contacting cartilage surrounding the acetabulum.

* * * * *